United States Patent [19]

Höht

[11] 4,123,934
[45] Nov. 7, 1978

[54] BRIDGE CIRCUIT ARRANGEMENT FOR A GAS DETECTION INSTRUMENT

[75] Inventor: Wolfgang Höht, Berlin, Fed. Rep. of Germany

[73] Assignee: Auergesellschaft GmbH, Berlin, Fed. Rep. of Germany

[21] Appl. No.: 808,140

[22] Filed: Jun. 20, 1977

[30] Foreign Application Priority Data

Jun. 22, 1976 [DE] Fed. Rep. of Germany ....... 2627916

[51] Int. Cl.² ........................................... G01N 27/18
[52] U.S. Cl. ............................. 73/27 R; 324/DIG. 1
[58] Field of Search .................. 73/27 R, 23, 204; 340/237 R; 23/232 E, 254 E; 324/62 R, DIG. 1

[56] References Cited

U.S. PATENT DOCUMENTS

| 3,678,489 | 7/1972 | Scherban et al. | 73/27 R |
| 3,879,717 | 4/1975 | Gruensfelder | 340/237 R |
| 4,007,456 | 2/1977 | Paige et al. | 340/237 R |

*Primary Examiner*—Stephen A. Kreitman
*Attorney, Agent, or Firm*—Brown, Flick & Peckham

[57] ABSTRACT

A bridge circuit is provided for a gas-detecting instrument of the type using an electrically-heated resistance element or filament as a sensing element. In order to prevent use of the instrument during the warmup period after initial energization, a portion of the bridge is short-circuited for a predetermined time after energization. The short-circuiting means is preferably a transistor connected across one of the arms of the bridge and controlled by a flip-flop with suitable time-delay circuits for switching the flip-flop.

1 Claim, 2 Drawing Figures

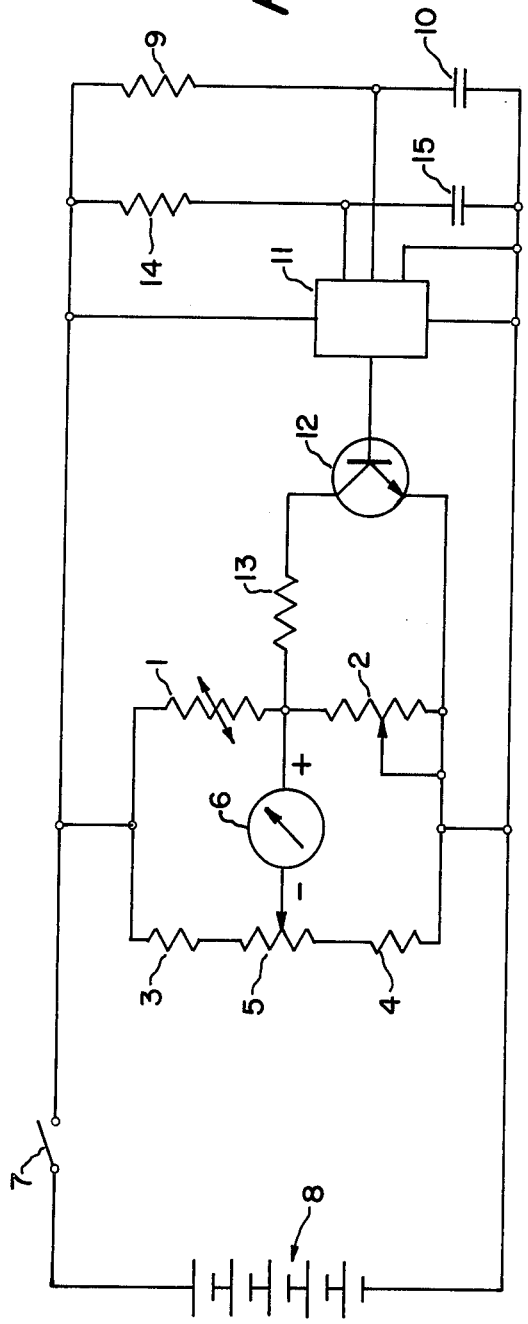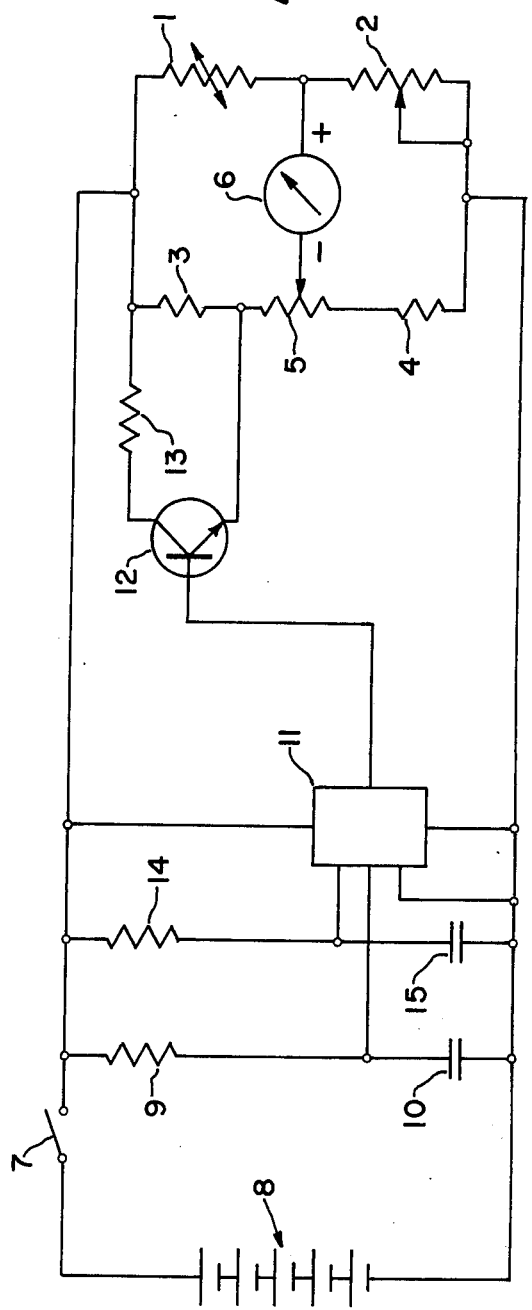

BRIDGE CIRCUIT ARRANGEMENT FOR A GAS DETECTION INSTRUMENT

BACKGROUND OF THE INVENTION

The present invention relates to bridge-type circuits using electrically-heated sensing elements for gas detection, and more particularly to means for altering the output signal in a predetermined manner during the warmup period following initial energization of the instrument.

Instruments of this type use an electrically-heated temperature-sensitive resistance element or filament as a sensing element, and observe changes in electrical resistance of the sensing element to detect gases or to measure such quantities as concentration of combustible gases. The sensing element is connected in a bridge circuit so that the change in resistance is detected as a voltage which can be applied to a suitable meter to read the desired quantity or, if desired, can be used to actuate an alarm or other signal. When such a heated sensing element is initially energized, a certain time is required for the filament to become heated and for its temperature to stabilize at the normal operating level. Any readings taken during this time, or any signals, may be erroneous or inconsistent because of the fact that the sensing element has not reached a stable equilibrium temperature. For this reason, it is desirable to prevent use of the instrument during this initial warmup period.

It has been proposed, as shown in German Pat. No. 1,263,329, to inhibit use of the instrument during the warmup period by switching a capacitor across the meter charged with opposite polarity to that of the bridge. This arrangement prevents the meter from giving a positive indication since it tends to cause the meter to deflect in the reverse direction to its normal indication. The capacitor is normally charged by the battery voltage which also energizes the bridge, and when the instrument is switched ON, the capacitor is switched across the meter by suitable control means such as a transistor. This prevents any initial positive swing by the meter, and inhibits use of the instrument since the meter does not give a normal reading. After the capacitor has discharged, the meter returns to normal use while the capacitor is reconnected to the battery. The discharge time is determined by the capacitance of the capacitor and the internal resistance of the meter, together with any necessary series resistance, and since a relatively long time constant may be needed, a high capacitance is required because the internal resistance of the meter is usually quite low. The required large capacitance makes it necessary to use an electrolytic capacitor which is undesirable. Another disadvantage of this arrangement is that accurate adjustment of the time period is not normally possible.

SUMMARY OF THE INVENTION

The present invention provides a circuit for instruments of the type described above using an electrically-heated sensing element connected in a bridge for detecting changes in resistance of the sensing element, and provides means for preventing use of the instrument for a predetermined time after initial energization to allow the sensing element to reach its normal operating temperature and to stabilize at that temperature.

In accordance with the invention, means are provided for short-circuiting one arm of the bridge immediately upon initial energization of the circuit so that extreme unbalance of the bridge results and the meter deflects in reverse direction to normal so that no reading can be obtained. After a predetermined time period which is long enough to allow the sensing element to become stabilized at its operating temperature, the short-circuit is removed and the instrument is ready for use. The short-circuiting means is preferably a transistor connected across one arm of the bridge and controlled by a flip-flop, or equivalent device, which turns the transistor ON upon energization of the circuit and which turns it OFF after a predetermined time. Suitable resistor-capacitor networks are used to control the operation of the flip-flop to turn the transistor ON and OFF at the desired times.

BRIEF DESCRIPTION OF THE DRAWING

The invention will be more fully understood from the following detailed description, taken in connection with the accompanying drawing, in which:

FIG. 1 shows an illustrative embodiment of the circuit of the present invention; and FIG. 2 shows an alternative circuit arrangement.

DESCRIPTION OF THE PREFERRED EMBODIMENT

As shown in FIG. 1 of the drawing, the circuit utilizes an electrically-heated temperature-sensitive resistance element or filament 1 which serves as the sensing element of the instrument. An adjustable resistor 2 is also provided which can be utilized as a calibrating or adjusting element to compensate for environmental influences other than those affected by the presence of the gas to be detected. The sensing element 1 and resistor 2 are connected in a bridge circuit with fixed resistors 3 and 4, as shown, and with an adjustable resistor 5 connected to a meter 6 across the diagonal of the bridge. The resistor 5 is utilized to balance the bridge at a desired value of resistance of the sensing element 1. The bridge may be energized by any suitable direct current source, shown as a battery 8, connected across the bridge by a switch 7. In operation, when the switch 7 is closed and the bridge is energized, the resistance of the sensing element 1 is affected by the presence of the gas to be detected, or by changes in the concentration of the gas if the meter is to be used for measuring concentrations, and such changes in resistance are detected as an unbalance of the bridge which can be read on the meter 6. The meter can, of course, be calibrated to show gas concentration, or it can be utilized to actuate an alarm or other type of signal to indicate the presence of a particular gas.

As previously discussed, when this circuit is initially energized by closure of the switch 7, a certain length of time is required for the sensing element 1 to heat up to its normal operating temperature and become stabilized at that temperature, and if it is attempted to use the instrument during this warmup period erroneous or inconsistent readings can be obtained or an alarm may be actuated incorrectly. In order to avoid this, it is desirable to disable the instrument, or at least to indicate that it is not to be used, during this time period. In accordance with the present invention this is accomplished by short-circuiting a portion of the bridge so that the meter 6 indicates an extreme unbalance, or preferably is deflected in the reverse direction to the normal deflection, so that no usable signal is obtained. For this purpose, a transistor 12 is preferably utilized having its emitter and collector connected in series with a current-limiting resistor 13 across one arm of the bridge such as the resistor 2. This arrangement is shown in FIG. 1 and is preferred when the resistance 2 is relatively high as compared to the resistance of the sensing element 1. With other types of sensing elements having different resistances, however, it may be desirable to connect the transistor 12 across the fixed resistor 3 diagonally opposite to resistor 2, as shown in FIG. 2, and if desired suitable switching means could be provided to change from one connection to the other in accordance with the type of sensing element to be used for a particular purpose.

The transistor 12 is controlled to short-circuit the bridge arm 2 or 3 for the necessary length of time and then to remove the short-circuit. Any suitable type of control device could be used for this purpose, but it is preferred to use a monostable multivibrator or flip-flop 11 of the toggle type. Only one output terminal of the flip-flop 11 is utilized which is connected to the base of the transistor 12. The flip-flop has the usual SET and RESET terminals and an intermediate toggle terminal. Operation of the flip-flop is controlled by a resistor-capacitor network 9–10 and a second resistor-capacitor network 14–15, both of which are connected across the battery 8 and connected to the flip-flop switching terminals as shown.

In the operation of this circuit, when the switch 7 is closed to energize the circuit, the sensing element 1, which is initially cold, starts to heat up. Simultaneously the flip-flop 11 is pulsed to cause it to switch to the set state with a positive output from its output terminal. This supplies sufficient base drive to the transistor 12 to make it conductive so that one arm of the bridge is short-circuited as previously described. After the lapse of a predetermined time period determined by the network 9–10, the center or toggle terminal of the flip-flop 11 is pulsed and switches the flip-flop to the opposite state with zero output. This makes the transistor 12 non-conductive and thus removes the short-circuit from the bridge so that it becomes fully operative. The network 14–15 controls the reset terminal of the flip-flop and keeps it acutated so that repetitive pulsing of the toggle terminal by the network 9–10 is ineffective and the flip-flop remains in its reset state with zero output. It can thus only be set by initial energization of the circuit through switch 7 after the circuit has been deenergized.

It will be seen that a relatively simple circuit is thus provided which has many advantages. The time period during which the instrument is disabled after initial energization is easily adjusted by proper selection of the resistors or capacitors of the timing networks and can readily be changed if desired. Since the resistors can be made relatively large, the capacitors may have low capacitance and it is not necessary to use electrolytic capacitors. The size and cost are thus kept low while great accuracy in adjustment of the time period is obtainable. By properly designing the bridge and short-circuiting only one arm, the magnitude of reverse deflection of the meter 6 during the warmup period can be accurately determined and kept small enough to prevent any risk of damage to the movement of the meter. The magnitude of the reverse deflection remains constant during the warmup period as it is not dependent on the discharge of a capacitor.

I claim as my invention:

1. In combination, a measuring instrument including an electrically-heated resistance sensing element, a plurality of constant resistors connected in a bridge circuit with said sensing element, the bridge circuit including means for measuring change in resistance of said sensing element, a transistor connected across one of said resistors, and control means for said transistor operative upon energization of the sensing element to make the transistor conductive for short-circuiting a portion of the bridge circuit and including time delay means to cause the transistor to revert to the non-conductive state after a predetermined time period to remove the short circuit, said control means comprising a toggle type flip-flop having a resistor-capacitor network to control the time of switching from one state to the other.

* * * * *